US010368754B2

(12) United States Patent
Pekander (10) Patent No.: US 10,368,754 B2
(45) Date of Patent: Aug. 6, 2019

(54) METHOD AND SYSTEM FOR MONITORING BLOOD PRESSURE

(71) Applicant: General Electric Company, Schenectady, NY (US)

(72) Inventor: Otto Valtteri Pekander, Helsinki (FI)

(73) Assignee: General Electric Company, Schenectady, NY (US)

( * ) Notice: Subject to any disclaimer, the term of this patent is extended or adjusted under 35 U.S.C. 154(b) by 121 days.

(21) Appl. No.: 15/271,310

(22) Filed: Sep. 21, 2016

(65) Prior Publication Data

US 2018/0078158 A1 Mar. 22, 2018

(51) Int. Cl.
*A61B 5/02* (2006.01)
*A61B 5/021* (2006.01)
*A61B 5/022* (2006.01)

(52) U.S. Cl.
CPC ...... *A61B 5/02141* (2013.01); *A61B 5/02233* (2013.01); *A61B 2560/0266* (2013.01); *A61B 2562/08* (2013.01)

(58) Field of Classification Search
CPC . A61B 5/02141; A61B 5/021; A61B 5/02233; A61B 2560/0266
See application file for complete search history.

(56) References Cited

U.S. PATENT DOCUMENTS

| 4,501,280 A | 2/1985 | Hood, Jr. | |
| 5,060,654 A | 10/1991 | Malkamaki et al. | |
| 6,231,517 B1* | 5/2001 | Forstner | A61B 5/02233 600/485 |
| 6,450,966 B1 | 9/2002 | Hanna | |
| 2002/0120201 A1* | 8/2002 | Chio | A61B 5/0002 600/490 |
| 2009/0099466 A1* | 4/2009 | Wong | A61B 5/02141 600/495 |
| 2010/0105531 A1* | 4/2010 | Crawford | A63B 21/00185 482/124 |
| 2010/0305633 A1* | 12/2010 | Aziz | A61B 5/0205 607/3 |
| 2011/0202495 A1* | 8/2011 | Gawlick | A61B 5/0002 706/59 |
| 2011/0245622 A1* | 10/2011 | McKenna | A61B 5/02416 600/300 |
| 2012/0089034 A1* | 4/2012 | Woehrle | A61B 5/022 600/493 |
| 2012/0259233 A1* | 10/2012 | Chan | A61B 5/0002 600/484 |
| 2013/0218033 A1* | 8/2013 | Quinn | A61B 5/02225 600/492 |
| 2016/0331245 A1* | 11/2016 | Herndon | A61B 5/02225 |
| 2017/0086677 A1 | 3/2017 | Pekander et al. | |

* cited by examiner

*Primary Examiner* — Navin Natnithithadha
*Assistant Examiner* — Andrey Shostak
(74) *Attorney, Agent, or Firm* — Andrus Intellectual Property Law, LLP (57) ABSTRACT

A system for monitoring blood pressure includes a blood pressure cuff, a blood pressure measurement device removably connected to the blood pressure cuff, and a cuff verification module. The cuff verification module is executable on a processor to receive medical record information from a patient, determine an expected cuff size for the patient based on the medical record information, receive a detected cuff size for the blood pressure cuff, and verify that the detected cuff size is consistent with the expected cuff size.

23 Claims, 5 Drawing Sheets

METHOD AND SYSTEM FOR MONITORING BLOOD PRESSURE

BACKGROUND

The subject matter disclosed herein relates to non-invasive blood pressure (NIBP) monitoring. More specifically, the present disclosure relates to an apparatus and system to identify and verify a blood pressure cuff size.

Automated blood pressure monitoring has rapidly become an accepted and central aspect of human health care. Such monitors are now a conventional part of patient monitoring, especially in clinics, emergency rooms, intensive and critical care units, and in the operating room. As no single cuff size is effective for all possible patients, cuffs of various sizes ranging from infant or child, to large adult are used. Additionally, blood pressure measurements may be obtained at different locations on the body, such as the thigh, and additional specially sized cuffs may be used in such applications. Using the properly sized blood pressure cuff is important because erroneous blood pressure measurements may result from using a cuff that is too large or too small.

Therefore, the appropriately sized cuff needs to be selected by the clinician and the cuff size needs to be accurately identified by the blood pressure measurement device. A reliable system and method for verifying a blood pressure cuff size is desired.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a system for monitoring blood pressure includes a blood pressure cuff, a blood pressure measurement device removably connected to the blood pressure cuff, and a cuff verification module. The cuff verification module is executable on a processor to receive medical record information from a patient, determine an expected cuff size for the patient based on the medical record information, receive a detected cuff size for the blood pressure cuff, and verify that the detected cuff size is consistent with the expected cuff size.

One embodiment of a method of monitoring blood pressure of a patient includes receiving medical record information for the patient and determining an expected cuff size for the patient based on the medical record information. A detected cuff size is received for the blood pressure cuff, and then the detected cuff size is compared to the expected cuff size to determine if the detected cuff size is consistent with the expected cuff size.

BRIEF DESCRIPTION OF THE DRAWINGS

The present disclosure is described with reference to the following Figures.

DETAILED DESCRIPTION OF THE DRAWINGS

In many blood pressure monitors, the cuff size must be manually set or selected by a clinician. In other devices, the cuff size may be automatically identified by various means, such as via RFID, flow resistors, by detecting cuff volume, or by visual detection of an identifier label on the cuff. However, the present inventor has recognized that each of these methods is flawed. Manual identification is ripe for user error. Automatic solutions can also make errors, and thus redundant systems are necessary in order to provide sufficient reliability and accuracy. However, each automatic solution adds to the price and the manufacturing process, and adds complexity and failure points to the blood pressure cuff. Moreover, some automatic solutions, such as flow resistors, have a negative impact on performance.

The inventor has also recognized that the misidentification of a blood pressure cuff could potentially lead to a hazardous situation, especially if the patient being measured is a neonate and the blood pressure cuff is misidentified as a much larger cuff (such as an adult-sized cuff). Accordingly, the inventor has recognized a need for systems and methods that verify cuff size detection, including automated cuff recognition, and that it is highly desirable to provide cuff size verification in a way that does not require additional hardware, which only adds to cost and creates an additional failure point.

In view of the foregoing recognition of needs and problems in the relevant art, the inventor has developed the method and system disclosed herein for noninvasively measuring blood pressure from a patient that utilizes the patient's medical record information as a basis for verifying cuff size. For example, the inventive system may utilize patient demographic information, such as age, weight, and/or height, to determine an expected cuff size for the patient. When a blood pressure cuff is detected as being connected to the blood pressure measurement device in use on the patient, the system checks the detected cuff size against an expected cuff size to verify that the detected cuff size is accurate. If the detected cuff size does not match the expected cuff size, then additional steps may be executed, in certain embodiments, to further check the cuff size and determine whether it is within an expected size range based on information available from the patient's medical record. For example, an inflation test may be performed where the blood pressure cuff is inflated with a predetermined amount of air and then the pressure change is measured to determine whether the pressure change is within a range that would be expected based on the expected cuff size. Alternatively or additionally, a maximum expected fill amount may be set based on the expected cuff size and the blood pressure cuff may be inflated in a careful manner and managed such that the cuff is not inflated beyond the maximum expected fill amount. Such methods and systems are described in more detail below with respect to the exemplary embodiments depicted in the Figures.

Figure 1:
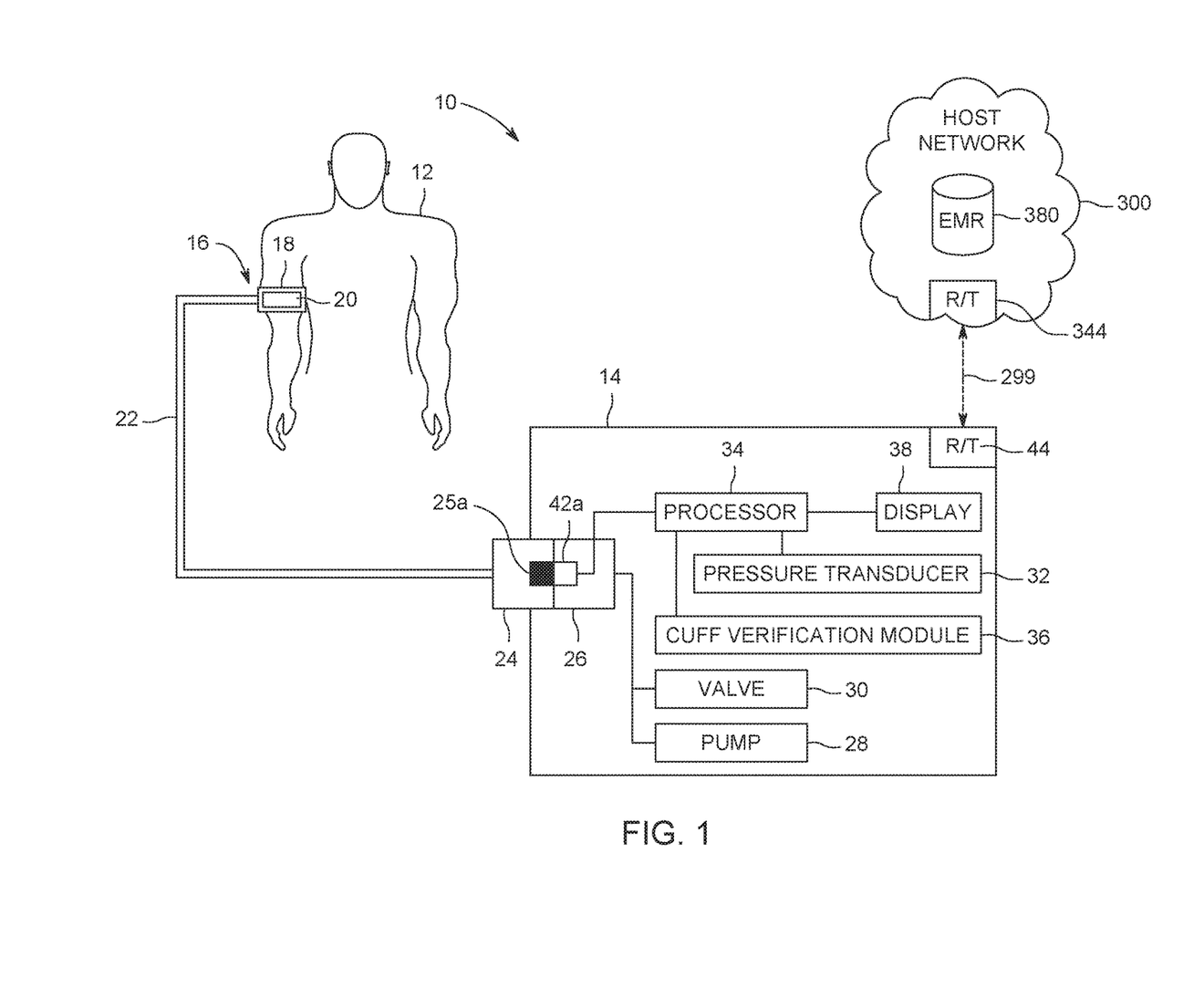
FIG. 1 is a schematic diagram of a non-invasive blood pressure measurement system attached to a patient in accordance with an embodiment of the present disclosure.

Referring to FIG. 1, a non-invasive blood pressure (NIBP) monitoring system 10 attached to a patient 12 is shown in accordance with an embodiment. The NIBP monitoring system 10 includes a blood pressure measurement device 14 releasably connected to a blood pressure cuff 16. The blood pressure cuff 16 includes a flexible band 18. The flexible band 18 is generally wrapped around a limb of patient 12. In FIG. 1, the limb is depicted as comprising the patient's upper arm, however, it should be appreciated that the flexible band 18 may alternatively be applied to other locations on the patient's arm (e.g., forearm) or to other limbs (e.g., leg).

The flexible band 18 includes an inflatable bladder 20. Although the cuff bladder 20 is shown as being an integral component of the flexible band 18, it should be appreciated that alternative blood pressure cuff configurations may include a separate inflatable cuff bladder.

The blood pressure cuff 16 may be provided in a variety of sizes to accommodate patients of varying sizes as well as different limbs upon which blood pressure monitoring is made. The blood pressure cuff size is based on the circumference of the patient limb around which the blood pressure cuff 16 is placed and corresponds to the length of the flexible band 18. For example, the blood pressure cuff size can range from a neonatal cuff size range—e.g., approximately 3 cm to 8 cm—to an infant cuff size range—e.g., approximately 7 cm to 15 cm—to a child cuff size range—e.g., approximately 12 cm to 21 cm—to an adult cuff size range—e.g., approximately 20 cm to 45 cm—to a thigh cuff size range—e.g., 40 cm to 60 cm. Additionally, within each cuff size range, there may be multiple cuff sizes. For example, there may be three different cuff sizes in the neonatal cuff size range: a small, medium and large. Each cuff size may be associated with a predetermined range of patient ages, sizes, and/or weights.

The blood pressure cuff 16 further comprises a flexible tube 22. Flexible tube 22 is operatively connected at a first end to the cuff bladder 20 and allows air to be pumped into, and released from cuff bladder 20. It should be appreciated that while a single flexible tube 22 is depicted in FIG. 1, the blood pressure cuff 16 may comprise two flexible tubes 22. In such an embodiment, a first flexible tube 22 would direct air into the cuff bladder 20, and while air would be released from the cuff bladder 20 via a second flexible tube 22.

The flexible tube 22 comprises a connector 24 at its second end. The connector 24 is configured to releasably mate with the blood pressure measurement device 14. In one embodiment, the connector 24 mates in a snap-fit manner with a connector 26 of the blood pressure measurement device 14. In another embodiment, the connector 24 mates in a force-fit manner with connector 26 of the blood pressure measurement device 14. It should be appreciated that the connectors 24 and 26 may releasably mate in other manners, such as a twist-fit manner, a leur locking or a leur slipping manner, within the scope of this disclosure. Connector 24 may be either a male or female connector within the scope of this disclosure and connector 26 would be the corresponding female or male connector.

The blood pressure measurement device 14 includes a pump 28 adapted to inflate the cuff bladder 20, and one or more valves 30 adapted to deflate the cuff bladder 20. The blood pressure measurement device 14 includes a pressure transducer 32 operable to sense or identify pressure pulses at the portion of the limb to which the blood pressure cuff 16 is attached. A processor 34 converts the pressure pulse data from the pressure transducer 32 into blood pressure data. The processor 34 may be a microprocessor and other circuitry that retrieves and executes software.

The blood pressure measurement device 14 is configured to measure mean arterial pressure (MAP), systolic blood pressure (SBP), and/or diastolic blood pressure (DBP) by inflating the blood pressure cuff bladder 20 to a suprasystolic pressure level and measuring oscillations under the blood pressure cuff bladder 20 as the cuff bladder 20 is deflated. For purposes of this disclosure, the term "oscillation" refers to a measurable pressure level pulse produced by a change in volume of an artery under the pressure cuff bladder 20.

Various means may be provided by which the blood pressure measurement device 14 may detect the cuff size of the blood pressure cuff 16. For example, the blood pressure cuff 16 may be provided with identifier means for identifying the cuff size and the measurement device 14 may be equipped with a corresponding detector means for detecting the identifier means, and thus for detecting the identified cuff size of the blood pressure cuff 16. In the embodiment depicted in FIG. 1, the identifier means are exemplified as an identifier chip 25a which communicates with a detector means that is a receiver 42a configured to receive communication from the identifier chip 25a.

In the depicted embodiment, the identifier chip 25a is located in the connector 24 and the receiver 42a is located in the connector 26 on the blood pressure measurement device 14. Thus, the identifier chip 25a is placed in close proximity to the receiver 42a when the connector 24 is connected to the connector 26. In other embodiments, the identifier chip 25a may be placed elsewhere on the blood pressure cuff 16, such as elsewhere on the connector 24, on the flexible tube 22, on the flexible band 18, or on the inflatable bladder 20. Likewise, the receiver 42a may be located anywhere on, in, or in proximity to the measurement device 14. For example, the receiver 42a may be on the measurement device 14 adjacent to or near the location of the connector 26.

In various embodiments, the identifier chip 25a may communicate with the receiver 42a according to any of various radio communication protocols, such as radio-frequency identification (RFID), near field communication (NFC), or the like. In various embodiments, the identifier 25a may be, for example, an active RFID chip that actively transmits radio communication to the receiver 42a, or the identifier chip 25a may be a passive RFID tag configured to be energized to communicate the cuff size identification when in proximity of the receiver 42a. The receiver 42a receives information from the identifier chip 25a related to the cuff size of the blood pressure cuff 16, and such information is transmitted to the processor 34 and will be received as the detected cuff size information 58 (see FIG. 3).

Figure 2:
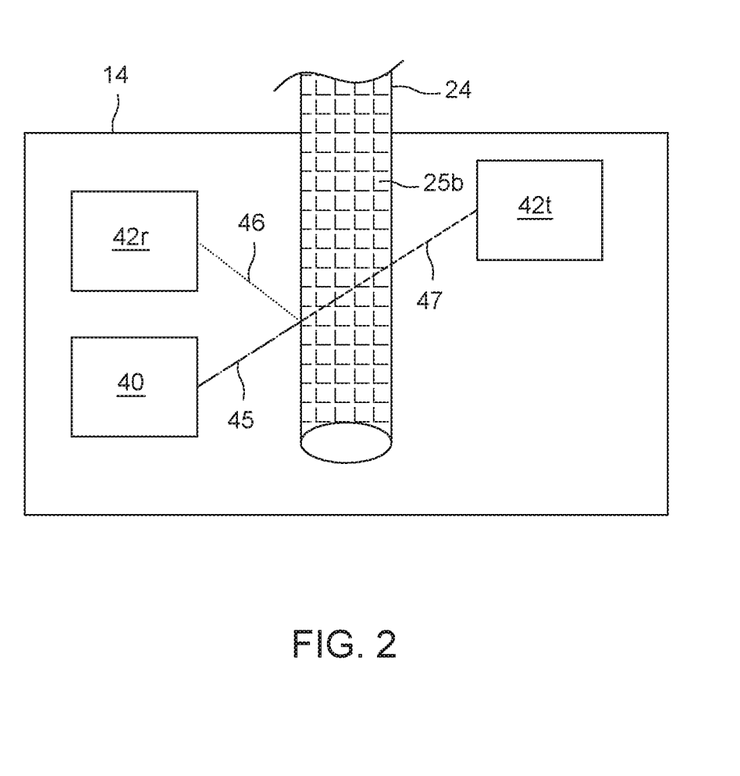
FIG. 2 is a schematic diagram of an exemplary means for identifying and detecting cuff size in accordance with one embodiment of the disclosure.

FIG. 2 depicts another embodiment of the means for detecting cuff size, which utilizes a detector means that optically detects an identifier label 25b associated with the blood pressure cuff 16. In the depicted embodiment, the identifier label 25b may be located anywhere on the blood pressure cuff 16, and the detector means may be positioned accordingly. In the embodiment of FIG. 2, the identifier label 25b is provided on the connector 24 that connects to the connector 26 of the blood pressure measurement device 14. Connector 24 may comprise an identifier label 25b, represented in FIG. 2 by crosshatching. The identifier label 25b corresponds to a blood pressure cuff size. In one embodiment, the identifier is a color in the visible range (approximately 380-800 nm) of the electromagnetic radiation spectrum. For example, identifier label 25b may be comprised of a colored plastic, nylon or other petroleum-based synthetic material, where the color indicates the blood pressure cuff size and is associated with that blood pressure cuff size by the system 10. Each of the various colors corresponds to a particular cuff size, and it should be appreciated that various other colors in the visible spectrum may be used to identify each cuff size of the possible cuff size identified by the system 10.

In another embodiment, the identifier label 25b is a coating. For example, a coating within the ultraviolet wavelength range may be applied to the connector 24. In another example, a coating within the infrared wavelength range may be applied to the connector 24. In yet another example, a coating within the visible wavelength range may be applied to the connector 24. As with the colors described above, a plurality of coatings may be used as identifiers, with each coating corresponding to a specific cuff size.

In yet another embodiment, the identifier label 25b is a surface texture. For example, the identifier may be a ridged texture with the peaks and valleys spaced at a specific interval. In another example, the identifier may be a honeycomb type texture. In yet another example, the identifier may be a perforated-type texture. Again, as with the colors described above, a plurality of textures may be used as identifiers, with each texture corresponding to a specific cuff size.

It should be appreciated that other types of identifiers or combinations thereof may be used to differentiate between cuff sizes. For example, the identifier may be a color-based pattern, which in certain embodiments could form a letter or number, or could be a barcode.

In the depicted embodiment utilizing optical recognition cuff detection means, where the identifier means is provided by the identifier label 25b, the detector means may be any means by which the identifier label 25b can be optically detected, such as by an optical sensor. In the depicted embodiment, the detection means is provided by two optical detectors 42r and 42t that detect radiation emitted by an emitter 40. For example, the emitter 40 may be an electromagnetic radiation emitter configured to direct radiation onto the identifier label 25b, such as on the connector 24 when the connector 24 is mated with the blood pressure measurement device 14. In one embodiment, the emitter 40 may be a light emitting diode (LED) that emits electromagnetic radiation in the visible wavelength spectrum (approximately 380-800 nm). In another embodiment, the emitter 40 may be a LED that emits radiation in the ultraviolet wavelength spectrum (approximately 10-400 nm). In yet another embodiment, the emitter 40 may be a LED that emits radiation in the infrared wavelength spectrum (approximately 700 nm-1 mm). It should be appreciated that various other embodiments of the emitter 40 may be envisioned within the scope of this disclosure. For example, the emitter 40 may be an RF source. In another example, the emitter 40 may be configured to emit radiation in a plurality of spectra such as the visible spectrum and the ultraviolet spectrum. In yet another example, the emitter 40 may be an ambient light source.

The blood pressure measuring device 14 also comprises one or more electromagnetic radiation detectors, which in the depicted embodiment include detectors 42r and 42t. The detectors 42r and 42t may be a photodetector or any other sensor configured to detect electromagnetic radiation from the emitter 40. In various embodiments, the detectors may detect radiation by reflection or absorption, or a combination thereof. In the example, the emitter 40 and detector 42r are placed on the same side with respect to the identifier label 25b, and thus the detector 42r is configured to detect radiation that is reflected off of the identifier label 25b. Where the emitter 40 and detector 42t are placed on opposing sides of the identifier label 25b, the detector 42t is configured to detect radiation by absorption.

Each detector 42r and 42t may be configured to detect electromagnetic radiation in a particular spectrum. For example, the detectors 42r and 42t may detect visible wavelength spectrum (approximately 380-800 nm), the ultraviolet wavelength spectrum (approximately 10-400 nm), or the infrared wavelength spectrum (approximately 700 nm-1 mm). The detectors 42r and 42t may detect radiation across a plurality of spectra.

Each detector 42r and 42t is configured to transmit a signal relating to the detected radiation to the processor 34. The processor 34 is configured to receive the signal from the detectors 42r and 42t and determine a detected cuff size for the blood pressure cuff 16 mated with the blood pressure measurement device 14 by executing computer-readable instructions.

In other embodiments, the means for indicating and detecting the cuff size may be acoustic volume measurement methods. In one embodiment, the cuff has two tubes that are connected to the cuff internal volume, each tube having a pressure sensor in it. The pump is connected to one of the tubes, which is used to inflate the cuff. The pressure sensor located in the same tube as the pump will see immediate increase in pressure when the pump is enabled; however, the sensor connected to other tube will see delayed increase of pressure. The cuff volume is determined based on the delay time between the pressure increase sensed in each the two tubes—i.e. how quickly the pressure wave propagates from the first pressure sensor to the second pressure sensor.

Another means for indicating and detecting the cuff size includes measuring the flow that goes to the cuff. The volume of the cuff is then determined based on the pressure curve—e.g. by measuring time how long the pump has to be on and/or how much air must be added to reach certain pressure change. In yet another embodiment known to a person having ordinary skill in the relevant art, each different cuff assembly may be provided with a corresponding gas-flow restrictor which allows the pressure measurement(s) made during deflation of a given cuff assembly to be correlated in fashion that allows for identification. In such an embodiment, first and second pressure transducers are provided for automatic pressure measurements both upstream and downstream of a cuff assembly during the deflation portion of a cuff identification operation. The upstream and downstream pressure measurements are utilized to calculate a sequence of ratio values which in turn may be employed in the cuff identification procedure to determine the cuff size.

In still other embodiments, the detected cuff size 58 (FIG. 3) may be received and/or determined based on input of a clinician, such as by a clinician inputting the cuff size into a user interface on the measurement device 14 and/or associated with the NIBP monitoring system 10. The detected cuff size 58 is then received at the processor 34, which executes instructions to verify the cuff size as described herein. For example, a cuff verification module 36 may be stored in memory, such as in memory within the measurement device 14, which is comprised of computer executable instructions or code, executable on the processor 34 to determine whether the detected cuff size 58 is consistent with an expected cuff size 62 for the particular patient 12.

More specifically, the cuff verification module 36 comprises instructions executable by the processor 34 to receive medical record information for the patient 12 and determine an expected cuff size 54 based thereon. The medical record information may be any information stored with respect to the patient 12 that could be relevant to determining an appropriate cuff size for non-invasively measuring the patient's blood pressure. Examples of such medical record information include, but are not limited to, the patient's age 50, height 51, or weight 52, and may also include information related to previous blood pressure measurements of the patient, including a previous cuff size 54 and historical blood pressure information 56 (see FIG. 3).

Figure 3:
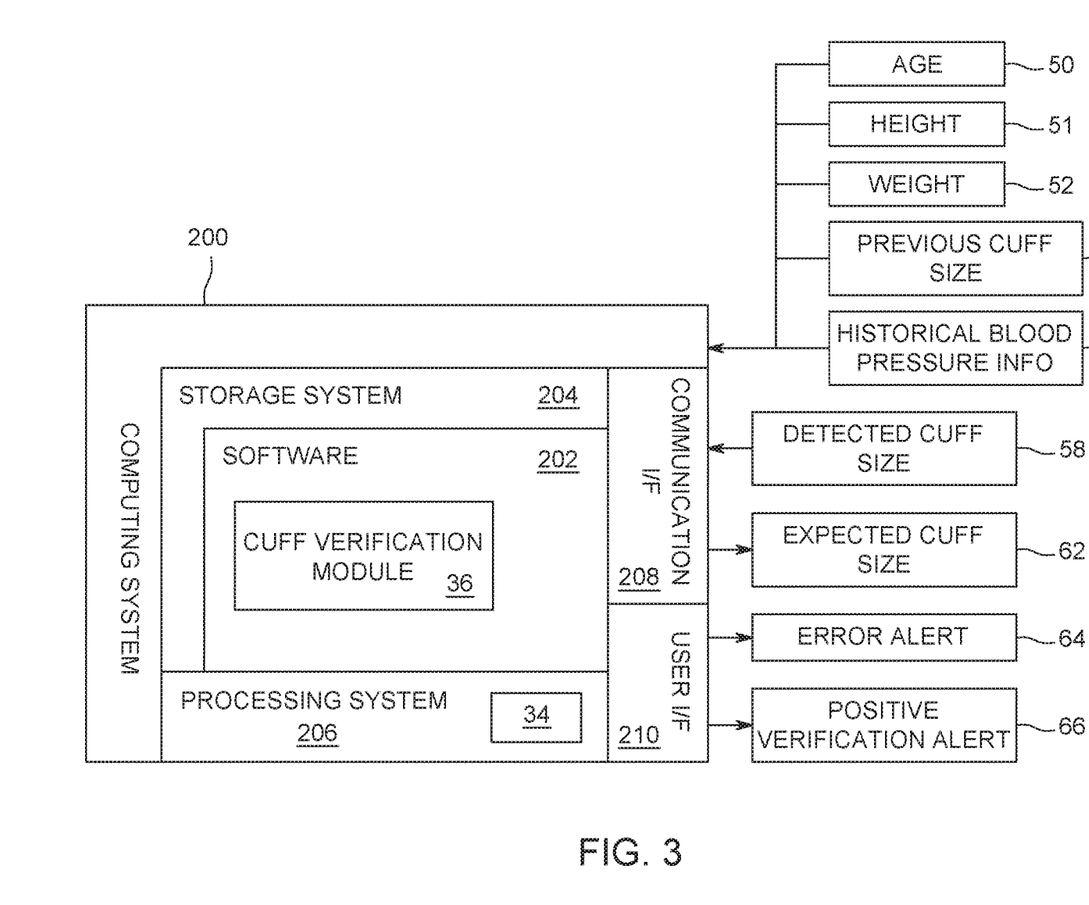
FIG. 3 is a schematic diagram of one embodiment of a computing system incorporated in a system for monitoring blood pressure in accordance with an embodiment of the disclosure.

The communication interface 208 interfaces between the elements within the computing system 200 and external devices, such as the pump 28, the valve 30, the pressure transducer 32, the display 38, the detector means 42, etc. The communication interface 208 may include the receiver/transmitter 44 that communicates with the host network 300 to obtain the patient's medical record information.

The computing system 200 may further include a user interface 210 configured to interface with a clinician or the patient, such as to receive inputs and display information. For example, the user interface 210 may include a display 38 on or associated with the measurement device 14, which in some embodiments may be any video display or touch screen. Speakers for producing audio output, printers, haptic devices and other types of output devices may also be included in the user interface 210. User interface 210 may further include input devices, such as a keyboard or keypad, a mouse, a voice input device, a touch input device for receiving a gesture from a user, a motion input device for detecting non-touch gestures and other motions by a user, and other comparable input devices and associated processing elements capable of receiving input from a user, such as a clinician.

Returning to the embodiment of FIG. 1, the measurement device 14 may be in data communication with a host network 300 via a communication link 299. Specifically, the measurement device 14 may include a receiver transmitter 44 configured to communicate with receiver transmitter 344 incorporated in the host network 300. Each of the receiver transmitters 44 and 344 may be any device capable of receiving and transmitting information, and may be comprised of separate receiving and transmitting devices, or may be a combined receiving and transmitting device or transceiver. The receiver transmitters 44 and 344 may be configured to communicate according to any number of radio protocols, such as WI-FI®, BLUETOOTH®, wireless medical telemetry system (WMTS), ANT, ZIGBEE® (or the like). The host network 300 is a computer network, such as a computer network of a medical facility or hospital. For example, the host network 300 may include one or more servers housed within a medical facility or in data communication of a medical facility, such as for a network of medical facilities, or it may be a cloud-based system hosted by a cloud computing provider. The host network may include an electronic medical records (EMR) database 380 where the patient's medical record information is stored. Accordingly, the measurement device 14 may obtain medical record information for the patient 12 from the patient's electronic medical record stored in EMR database 380 via wireless communication with the host network 300. For example, patient identification information may be provided to the measurement device 14 prior to initiating blood pressure monitoring for the patient 12, such as by a clinician inputting the patients identification information into a user interface 210 of the measurement device 14. In still other embodiments, the measurement device 14 may be part of a larger patient monitoring system which may be networked to a hub device and/or to other medical monitoring devices, such as one of a set of body area network (BAN) devices, such as a medical body area network (MBAN) that operate as a wireless network of wearable or portable patient monitoring devices. Likewise, the measurement device 14 depicted in FIG. 1 may, in various embodiments, be embodied in two or more separate devices, such as a hub device in wireless communication with a wearable computing device attached to or in close proximity to the location of the blood pressure cuff 16 on the patient 12.

FIG. 3 provides a system diagram of an exemplary computing system 200 which may be incorporated into the NIBP monitoring system 10. For example, the computing system may be incorporated in the measurement device 14, or portions of the computing system may be contained in each of a hub device and a wearable computing device on or near the blood pressure cuff 16. The computing system 200 incorporates the processor 34 and the cuff verification module 36, and is in data communication with the various elements of the NIBP monitoring system 10 in order to carry out the blood pressure monitoring methods described herein.

The computing system 200 includes a processing system 206, storage system 204, software 202, communication interface 208 and a user interface 210. The processing system 206 loads and executes software 202 from the storage system 204, including the cuff verification module 36, which is an application within the software 202. The cuff verification module 36 includes computer-readable instructions that, when executed by the computing system 200, direct the processing system 206 to operate as described in herein in further detail, including to execute the steps to determine an expected cuff size 62 and determine whether the detected cuff size 58 is consistent therewith.

Although the computing system 200 as depicted in FIG. 3 includes one software 202 encapsulating one cuff verification module 36, it should be understood that one or more software elements having one or more modules may provide the same operation. Similarly, while the description refers to one computing system 200 and one processing system 206, it is to be recognized that implementations of such systems can be performed using one or more processors, which may be communicatively connected, and such implementations are considered to be within the scope of the description.

The processing system 206 includes the processor 34, which may be a microprocessor, a general purpose central processing unit, and application-specific processor, a microcontroller, or any other type of logic-based device. The processing system 206 may also include circuitry that retrieves and executes software 202 from storage system 204. Processing system 206 can be implemented within a single processor 34, but can also be distributed across multiple processing devices or sub-systems that cooperate in executing program instructions.

The storage system 204 can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. Storage system 204 may further include additional elements, such a controller capable of communicating with the processing system 206.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

Figure 4:
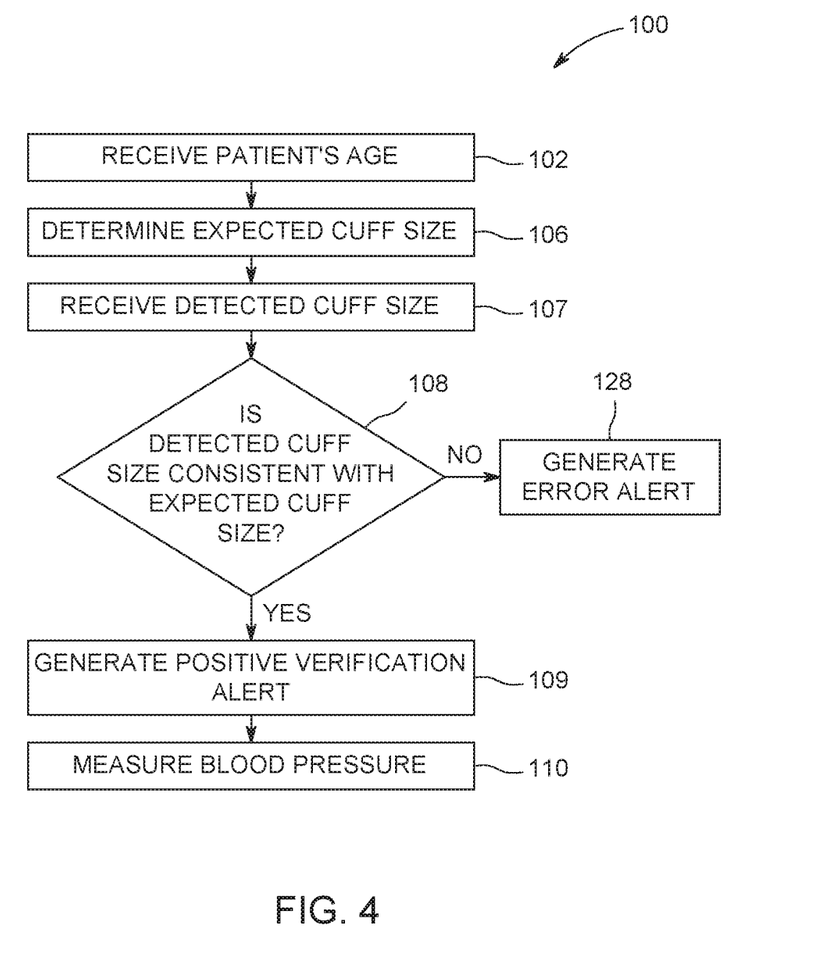
FIG. 4 is a flowchart depicting one embodiment of a method of monitoring blood pressure.
Figure 5:
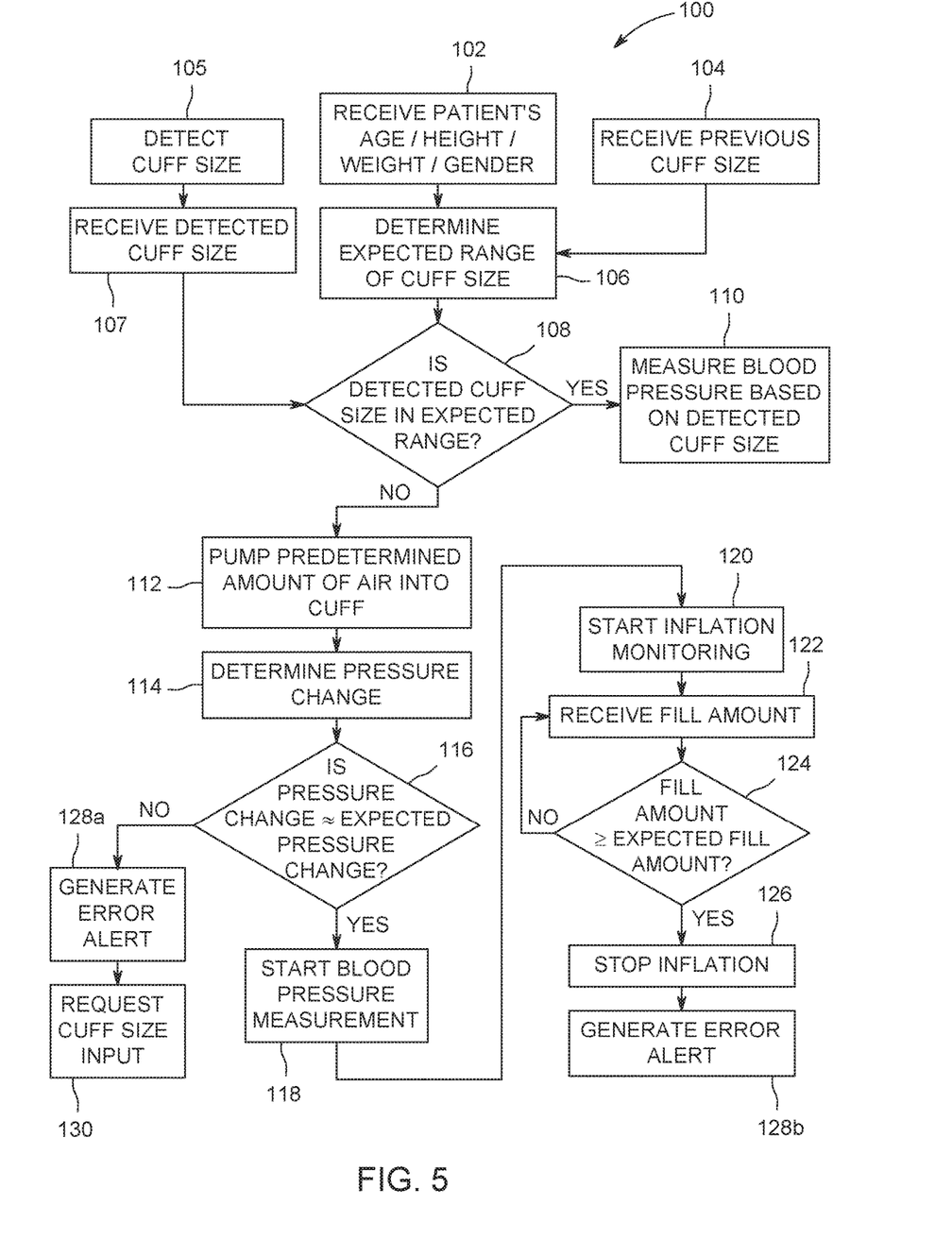
FIG. 5 is a flowchart depicting another embodiment of a method of monitoring blood pressure.

FIGS. 4 and 5 depict embodiments of a method 100 of monitoring blood pressure, such as including steps that may be carried out by executing instructions of the cuff verification module 36. In the embodiment of FIG. 4, a patient's age is received at step 102. An expected cuff size is determined at step 106 based on the patient's age. For example, the expected cuff size may be selected from a list of available cuff sizes, where each cuff size in the list of cuff sizes is associated with an age range. Furthermore, the age ranges assigned to each cuff may be overlapping, and thus the expected cuff size may include multiple cuff sizes or a range of cuff sizes. A detected cuff size is received at step 107, and step 108 determines whether the detected cuff size is consistent with an expected cuff size. For example, the cuff verification module 36 may contain instructions to determine whether the detected cuff size is equal to a particular expected cuff size based on the patient's age, or whether it is within a predetermined range of cuff sizes that could be appropriate for individuals of the patient's age group.

If the detected cuff size is consistent with the expected cuff size, then a positive verification alert may be generated at step 109. For example, the positive verification alert may be a visual and/or audio alert produced by the user interface 210 associated with the measurement device 14. For instance, the positive verification alert may be a notification provided on the display 38 notifying the clinician that the blood pressure cuff 16 was accurately detected. The system 10 may then proceed to measure the patient's blood pressure at step 110, such as by controlling the pump 28, valve 30, and pressure transducer 32 as described herein.

If it is determined at step 108 that the detected cuff size is not consistent with the expected cuff size, then an error alert may be generated at step 128, such as an audio or visual alert produced by the user interface 210. For example, the error alert may include an audio alarm produced by a speaker on or associated with the measurement device 14 and/or a visual alert on the display 38 alerting the clinician that there has been an error in detecting the blood pressure cuff 16. In other embodiments, additional steps may be executed in the event that the detected cuff size is not consistent with the expected cuff size such as to detect an inflation test. An example of such an embodiment is provided at FIG. 5.

In the embodiment of FIG. 5, the method 100 includes receiving medical record information relating to demographics for the patient at step 102, such as the patient's age, weight, height, gender, etc. Further medical record information is received at step 104, where a previous cuff size for the patient is received. For example, the previous cuff size may be a cuff size, or cuff size range, utilized for the patient to obtain a previous blood pressure measurement at another time in the patient's treatment history. For example, the previous cuff size information may be contained as part of a blood pressure history for the patient.

An expected cuff size is determined at step 106, which in the depicted embodiment is an expected range of cuff sizes, based on the information received at steps 102 and/or step 104. For example, the expected range of cuff sizes may be determined based on the patient's demographic information received at step 102, such as their age, weight, and height. For example, each cuff size in a list of available cuff sizes may be associated with a height and weight range. In another example, a range of cuff sizes may be provided based only on the patient's age. For example, if the patient is in a neonate age range, the neonatal cuff size range may be identified; if the patient is in an infant or child age range, then an infant or child cuff size range may be assigned; if the patient is in an adolescent age range or is above an adult age threshold, then an adult cuff size range may be assigned. The age, height, and/or weight ranges assigned to each cuff size in the list of possible cuff sizes may be overlapping, and thus multiple cuff sizes may be determined to be appropriate for any particular height and weight and each such cuff size may be included in the expected range of cuff sizes.

Similarly, the expected range of cuff sizes may be identified in a way that accounts for the previous cuff size assigned to the patient. For example, steps may be executed to determine whether the previous cuff size received at step 104 is within the expected range of cuff sizes determined based on the patient's demographic information. If not, then the expected range of cuff sizes may be expanded to include the previous cuff size, or alternatively an error could be generated. For example, the patient may have a medical history that suggests alternative placement of the blood pressure cuff rather than at the standard upper arm location. For example, if the previous cuff size is a thigh cuff size, then the expected range of cuff sizes may be assigned as a range of thigh cuff sizes, or at least expanded to include the range of thigh cuff sizes.

A cuff size is detected at step 105, such as utilizing any of the cuff size detection means described above. For example, the computing system 200 may further include a cuff size detection module comprised of computer executable instructions that, when executed, cause the measurement device 14 to detect a size of the blood pressure cuff 16. The detected cuff size is received at step 107, such as by the cuff verification module 36. Step 108 is then executed to determine whether the detected cuff size is within the expected range of cuff sizes. If the detected cuff size is within the expected range, then step 110 is executed to initiate measurement of the patient's blood pressure based on the detected cuff size. If the detected cuff size is not within the expected range, then additional steps may be executed in an attempt to verify whether the detected cuff size is accurate, and is actually the size of the blood pressure cuff 16 on the patient 12.

In the embodiment of FIG. 5, step 112 is executed to pump a predetermined amount of air into the blood pressure cuff 16. For example, the pump may be controlled to pump air at a predetermined pressure for a predetermined amount of time. At step 114 a pressure change resulting from the insertion of the predetermined amount of air into the cuff is determined. For example, an initial pressure measurement prior to executing step 112 may be compared to a pressure measurement after executing step 112. Step 116 is then executed to determine whether the pressure change is approximately equal to an expected pressure change for a particular expected cuff size or range of cuff sizes. For example, execution of step 116 may be intended to identify situations where the detected cuff size is way different than the expected cuff size, such as where an adult cuff size is detected but the expected cuff size is a neonatal cuff size or a neonatal cuff size range. If the pressure change is not approximately equal to or within a predetermined range of the expected pressure change, then an error alert may be generated at step 128*a*, such as an alert to the clinician of the problem. Additionally, a request may be produced requesting that the clinician identify the proper cuff size, such as to utilize the user interface 210 to input the actual cuff size of the blood pressure cuff 16.

If at step 116 the pressure change is within a predetermined range of the expected pressure change, then a blood pressure measurement may be initiated at step 118. As an extra precaution, additional instructions may be executed to prevent a potential hazardous situation, such as overinflating a cuff on a neonate or an infant and causing injury. In the depicted embodiment, an inflation monitoring protocol is started at step 120 where the amount of air pumped into the blood pressure cuff is monitored to ensure that an expected fill amount based on the expected range of cuff sizes is not exceeded. A fill amount is received at step 122, which in various embodiments could be a volume of gas pumped into the blood pressure cuff 16, or a gas pressure and time increment. In one embodiment, continual pressure measurements or volume amounts may be received over time and the cuff verification module 36 may integrate those amounts to determine the total fill amount. Step 124 is executed to determine whether the fill amount is equal to or exceeds an expected fill amount. The expected fill amount may be an assigned value based on the expected range of cuff sizes. To provide just one example, the expected fill amount may be equal to the largest inflatable bladder volume of the largest cuff in the expected range of cuff sizes. If the fill amount is equal to or greater than the expected fill amount, then the inflation is stopped at step 126, such as stopping operation of the pump 28. Alternatively or additionally, the valve 30 may be opened to immediately relieve pressure from the blood pressure cuff 16. An error alert is generated at step 128*b* to provide notification of the identified problem.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A system for monitoring blood pressure, the system comprising:
    a blood pressure cuff;
    a blood pressure measurement device removably connected to the blood pressure cuff; and
    a cuff verification module executable on a processor to perform cuff verification, including:
        receiving medical record information for a patient, wherein the medical record information includes an age of the patient;
        for each cuff verification, calculating an expected cuff size for the patient based on the age of the patient obtained from the medical record information;
        receiving a detected cuff size for the blood pressure cuff;
        verifying that the detected cuff size is consistent with the expected cuff size; and
        controlling inflation of the blood pressure cuff based on the expected cuff size.

2. The system of claim 1, wherein the cuff verification module is further executable on the processor to generate an error alert if the detected cuff size is not consistent with the expected cuff size.

3. The system of claim 1, wherein the expected cuff size is a range of cuff sizes based on the age of the patient, and the cuff verification module verifies that the detected cuff size is within the range of cuff sizes.

4. The system of claim 3, wherein the range of cuff sizes is one of a neonatal cuff size range, an infant cuff size range, and an adult cuff size range.

5. The system of claim 1, wherein the medical record information further includes one or both of a height and weight of the patient, wherein the cuff verification module is further configured to select the expected cuff size from a list of possible cuff sizes accessible by the cuff verification module based on the age of the patient and at least one of the height and weight of the patient, wherein each possible cuff size in the list of possible cuff sizes is associated with two or more of an age range, a height range, and a weight range.

6. The system of claim 1, wherein the medical record information further includes previous cuff size for the patient, and wherein the expected cuff size is determined based further on the previous cuff size.

7. The system of claim 1, wherein the cuff verification module is further configured to:
    control the blood pressure measurement device to pump a predetermined amount of air into the blood pressure cuff and measure a pressure change in the blood pressure cuff;
    compare the pressure change with an expected pressure change for the expected cuff size; and
    generate an error alert if the pressure change is not within a predetermined range of the expected pressure change.

8. The system of claim 1, wherein the cuff verification module is further configured to:
    determine a maximum expected fill amount based on the expected cuff size;
    control the blood pressure measurement device such that an amount of air pumped into the blood pressure cuff does not exceed the maximum expected fill amount.

9. The system of claim 1, wherein the cuff verification module is stored on memory in the blood pressure measurement device and the processor is contained in the blood pressure measurement device.

10. The system of claim 1, further comprising identifier means for identifying a cuff size of the blood pressure cuff, and detector means for detecting the identifier means.

11. A method of monitoring blood pressure of a patient, the method comprising:
    receiving medical record information for the patient at a processor of a blood pressure measurement device, wherein the medical record information includes an age of the patient;
    performing a cuff verification process, including, for each cuff verification:
        calculating, at the processor, an expected cuff size for the patient based on the age of the patient obtained from the medical record information;
        receiving, at the processor, a detected cuff size of a blood pressure cuff for use on the patient;

comparing, at the processor, the detected cuff size to the expected cuff size; and verifying, at the processor, that the detected cuff size is consistent with the expected cuff size; and controlling inflation of the blood pressure cuff by the blood pressure measurement device based on the expected cuff size.

12. The method of claim 11, further comprising generating a positive verification alert if the detected cuff size is consistent with the expected cuff size, or generating an error alert if the detected cuff size is not consistent with the expected cuff size.

13. The method of claim 11, further comprising, if the detected cuff size is consistent with the expected cuff size, automatically inflating the blood pressure cuff to measure a blood pressure of the patient.

14. The method of claim 12, wherein the expected cuff size is a range of cuff sizes based on the age, and wherein the detected cuff size is determined to be consistent with the expected cuff size if the detected cuff size is within the range of cuff sizes.

15. The method of claim 11, wherein the medical record information further includes one or both of a height and a weight of the patient.

16. The method of claim 15, wherein the step of determining the expected cuff size includes selecting, at the processor, from a list of possible cuff sizes stored in a storage system of the blood pressure measurement device based on the age and at least one of the height and the weight of the patient, wherein each possible cuff size in the list of possible cuff sizes is associated with two or more of an age range, a height range, and a weight range.

17. The method of claim 11, further comprising:

controlling the blood pressure measurement device to pump a predetermined amount of air into the blood pressure cuff and measure a pressure change in the blood pressure cuff;

comparing the pressure change with an expected pressure change for the expected cuff size; and generating an error alert if the pressure change is not within a predetermined range of the expected pressure change.

18. The method of claim 11, further comprising:

determining a maximum expected fill amount based on the expected cuff size; and controlling the blood pressure measurement device such that an amount of air pumped into the blood pressure cuff does not exceed the maximum expected fill amount.

19. A system for monitoring blood pressure, the system comprising:

a blood pressure cuff;

a blood pressure measurement device removably connected to the blood pressure cuff; and a cuff verification module executable on a processor to perform cuff verification, including:

receiving medical record information for a patient, wherein the medical record information includes at least one of an age, a height, and a weight of the patient;

for each cuff verification, calculating an expected cuff size for the patient based on the at least one of the age, the height, and the weight obtained from the medical record information;

receiving a detected cuff size for the blood pressure cuff;

verifying that the detected cuff size is consistent with the expected cuff size; and controlling inflation of the blood pressure cuff based on the expected cuff size.

20. The system of claim 19, wherein the cuff verification module is stored on memory in the blood pressure measurement device and the processor is contained in the blood pressure measurement device.

21. The system of claim 19, wherein the cuff verification module is further executable on the processor to generate an error alert if the detected cuff size is not consistent with the expected cuff size.

22. The system of claim 19, wherein the expected cuff size is a range of cuff sizes based on the age of the patient, and the cuff verification module verifies that the detected cuff size is within the range of cuff sizes.

23. The system of claim 19, wherein the cuff verification module is further configured to:

determine a maximum expected fill amount based on the expected cuff size; and control the blood pressure measurement device such that an amount of air pumped into the blood pressure cuff does not exceed the maximum expected fill amount.

\* \* \* \* \*